United States Patent [19]
Robinson

[11] Patent Number: 6,165,710
[45] Date of Patent: Dec. 26, 2000

[54] METHOD FOR IMMOBILIZING VIRAL GLYCOPROTEINS FOR USE IN SOLID-PHASE IMMUNOASSAYS

[76] Inventor: James E. Robinson, 2703 Camp St., New Orleans, La. 70130

[21] Appl. No.: 07/693,055

[22] Filed: Apr. 30, 1991

Related U.S. Application Data

[63] Continuation of application No. 07/424,930, Oct. 23, 1989, abandoned.

[51] Int. Cl.[7] ............................ C12Q 1/68; G01N 33/53; G01N 33/564; G01N 33/566
[52] U.S. Cl. ...................... 435/5; 435/7.1; 435/287.2; 435/974; 435/969; 530/350; 530/389.4; 530/806; 436/501; 436/172; 436/827
[58] Field of Search ............................ 435/5, 7.1, 287.2; 530/350, 389.4, 806; 436/531, 827, 501, 172; 424/89, 974, 969

[56] References Cited

U.S. PATENT DOCUMENTS

| | | | |
|---|---|---|---|
| 3,994,870 | 11/1976 | Neurath | 530/380 |
| 4,371,515 | 2/1983 | Chu | 436/544 |
| 4,374,127 | 2/1983 | Larson et al. | 424/89 |
| 4,426,871 | 1/1984 | Avrameas | 72/141 |
| 4,452,734 | 6/1984 | Larson | 530/395 |
| 4,470,967 | 9/1984 | Gough et al. | 424/89 |
| 4,478,946 | 10/1984 | Van der Merwe | 435/7.92 |
| 4,493,793 | 1/1985 | Chu | 530/303 |
| 4,532,232 | 7/1985 | Larson | 502/403 |
| 4,571,382 | 2/1986 | Adachi | 435/7.23 |
| 4,693,985 | 9/1987 | Degen | 436/531 |
| 4,695,537 | 9/1987 | Dorsett | 435/5 |
| 4,725,669 | 2/1988 | Essex | 530/322 |
| 4,743,678 | 5/1988 | Essex | 530/350 |
| 4,843,011 | 6/1989 | Sarngadharan et al. | 435/7 |
| 4,874,813 | 10/1989 | O'Shannessey | 525/54.1 |
| 4,877,725 | 10/1989 | Neurath et al. | 435/5 |
| 5,242,799 | 9/1993 | Samuel et al. | 435/7.1 |
| 6,030,772 | 2/2000 | Devico et al. | 435/5 |

FOREIGN PATENT DOCUMENTS

| | | |
|---|---|---|
| 0166623 | 1/1986 | European Pat. Off. . |
| 02880931 | 10/1988 | European Pat. Off. . |
| 034159 | 12/1989 | European Pat. Off. . |
| 0354200 | 2/1990 | European Pat. Off. . |
| 153 392 | 3/1985 | Germany . |
| WO86/02383 | 4/1986 | WIPO . |
| WO86/02930 | 5/1986 | WIPO . |
| WO87/07647 | 12/1987 | WIPO . |

OTHER PUBLICATIONS

Kalyanaraman et al., *AIDS Research and Human Retroviruses*, 4:319–329, 1988.
Kenealy et al., *AIDS Research and Human Retroviruses*, 3:95–104, 1987.
Lotan and Nicolson, *Biochimica et Biophysica Acta*, 559:329–376, 1979.
Mattes et al., *Journal of Immunological Methods*, 61:145–150, 1983.
Moore and Jarrett, *AIDS Research and Human Retroviruses*, 4:369–379, 1988.
Moore et al., *AIDS*, 3:155–163, 1989.
Robinson and Stevens, *Clinical Immunology and Immunopathy*, 33:339–350, 1984.
Salonen and Vaheri, *Journal of Immunological Methods*, 30:209–218, 1979.
Suter et al., *Journal of Immunological Methods*, 39:407–411, 1980.
Zwaagstra et al., *Journal of Virological Methods*, 20:21–32, 1988.

*Primary Examiner*—Bradley L. Sisson
*Attorney, Agent, or Firm*—Garvey, Smith, Nehrbass & Doody, L.L.C.

[57] ABSTRACT

A process for selectively immobilizing viral glycoproteins on lectin-coated surfaces for use in solid phase immunoassays is disclosed. This method does not require that the virus or antigen be purified prior to immobilization. This method provides an inexpensive and effective immunoassay method to screen fluids for the presence of viral antibodies.

26 Claims, No Drawings

METHOD FOR IMMOBILIZING VIRAL GLYCOPROTEINS FOR USE IN SOLID-PHASE IMMUNOASSAYS

This is a continuation of application Ser. No. 07/424,930 filed on Oct. 23, 1989, abandoned.

GOVERNMENT INT

This invention was made with Government support under the National Institutes of Health awarded by contract AI/24030. The Government has certain rights in the invention.

FIELD OF THE INVENTION

This invention relates to a process for selectively immobilizing viral glycoproteins on surfaces for use in novel, solid phase immunoassays to measure or detect antibodies to viral glycoproteins including HIV-1, HIV-2 and HTLV-1.

BACKGROUND OF THE INVENTION

Antigen Immobilization

It is a general principle of solid phase immuncassays that most water soluble proteins will bind irreversibly to certain types of plastic, particularly specially formulated polystyrene. However, the protein binding capacity of the plastic is very small. The purity of a protein and its absolute concentration in a mixture of proteins will determine if that protein will bind to a plastic surface in sufficient quantity to be useful as a solid phase antigen. Therefore, many proteins must be purified and concentrated prior to binding to a plastic surface for use as antigens in a solid phase immunoassay.

A plastic surface may first be coated with an antibody or other protein to enhance binding of the antigen of interest. (Moore et al, AIDS, 4:155–163, 1989.) In this type of "sandwich" immunoassay, an antibody is first passively coated to a plastic surface and then reacted with a solution containing the antigen of choice. Antigen thus immobilized is used in an immunoassay to detect antibodies in sera or other body fluids and tissue culture fluids. The immobilizing or "capture" antibody should not bind to the same antigenic sites to which the test antibodies are expected to bind.

Another coating substance by which antigens may be immobilized on plastic surfaces is Poly-L-Lysine (PLL). However, PLL, like plastic alone, is not able to select the type of proteins that are immobilized. Thus, prior to using PLL, the antigen of choice must be highly purified.

Solid Phase Immunoassays to Detect Antibodies to Viral Antigens

Today's research scientists and physicians require rapid, accurate and inexpensive methods to detect antibodies to a variety of viruses. In order to prepare assay kits for the marketplace, it is necessary to produce sufficient quantities of viral antigens. However, relatively small amounts of virus (particularly human retroviruses) are released in cultures of cells infected with the viruses. To obtain the quantities of virus antigens required to prepare large numbers of passively coated plastic surfaces, it is necessary to grow very large quantities of virus infected cells in tissue culture and then to separate the virus particles from the other protein constituents of the culture medium, especially the protein-rich serum used in the medium.

An additional consideration is the protein distribution of the virus particles. For example, The predominant protein species of retroviruses such as HIV-1 are found in the viral core, however the relatively minor glycoproteins found in the viral envelope are much more immunogenic. (Kalyanaraman et al, AIDS Research & Human Retroviruses, 4:319–329, 1988.) During the procedures of purification and inactivation of human retroviruses, a large proportion of the highly aritigenic envelope glycoprotein component is lost. (Moore et al, AIDS, 3:155–163, 1989.) Therefore, coating procedures which utilize purified retrovirus (such as HIV-1) provide relatively more core antigens than envelope antigens for immobilization. Moreover, no process to date has been able to completely purify virus from non-viral cellular proteins. Contaminating proteins, including histocompatibility antigens, may be co-purified with the virus and may passively bind to plastic surfaces. Such contaminants account for some of the false positive reactions obtained in serologic testing using these methods.

Because in general only small quantities retroviruses are released into the culture medium by infected cells, large amounts of virus producer cells must be grown in order to produce commercially useful quantities of concentrated, purified virus needed for making passively coated, solid phase immunoassays. For example, as much as 10–100 liters of virus-producing cells infected with human retroviruses such as HIV-1 or HTLV-I are typically needed to produce commercially useful quantities of antigens. Producing and processing such volumes of these viruses is both expensive and potentially biohazardous.

Recombinant DNA techniques may also be used to produce large amounts of virus encoded antigens. However, these antigens must still be purified from their producing cells before they can be passively absorbed to plastic surfaces creating similar problems as discussed above. The production of recombinant proteins is also expensive.

The available methods for producing viral antigens needed for solid phase immunoassays to detect antibodies against viruses such as HIV-1, HIV-2 and HTLV-1 require costly materials, costly processing, and considerable biohazards. The antigenic end-product provided by these methods is an antigen preparation containing a disproportionate amount of core antigens relative to the more desirable envelope glycoprotein antigens. In addition, the direct coating technique offers little control over which viral proteins become immobilized, and thus over the nature of the immunoassay.

It would be of great utility to provide a method to selectively immobilize viral glycoproteins which does not require that the virus be purified before coating the solid phase; which does not require large quantities of virus-producing cultures; which is inexpensive; and which provides immobilized viral antigen, for solid phase immunoassays that perform as well as or better than existing methods; and which requires no special procedures or equipment.

SUMMARY OF THE INVENTION

The present invention is a method for preparing solid-phase viral glycoproteins for use in immunoassays to detect virus-specific antibodies. This method utilizes lectin-coated surfaces to immobilize viral glycoproteins.

In the method of this invention, an assay surface is passively or covalently coated with lectin. The lectin serves to selectively immobilize viral glycoproteins contained in serum-free conditioned medium of virus-producing cell cultures. Such immobilized viral glycoproteins retain their function as antigens and are useful in immunoassays to detect viral glycoprotein-specific antibodies.

This method does not require that the virus be purified prior to coating the solid phase or assay surface; does not require large quantities of virus-producing cultures; is inexpensive; provides immobilized viral antigens for solid phase immunoassays that perform as well as or better than existing methods; and requires no special equipment or procedures.

DETAILED DESCRIPTION OF THE PREFERRED EMBODIMENTS

Production of Virus

Continuous cell lines, chronically and productively infected with the virus of choice are maintained in a suitable growth medium such as RPMI 1640 containing 10% fetal calf serum and the like culture medium. Preferred cell lines for producing virus such is HIV-1 and HIV-2 are continuous lymphoid cell lines which include, but are not limited to continuous T cell lines Each as H9, CEM, and MOLT 4 (available from The American Type Tissue Connection). Virus-transformed cell lines such as; MT2 which produces HTLV-I and MO which produces HTLV-II may also be used as a source of their respective viruses. In general, any infected cell line which can grow and produce the infected virus may be used in the method of this invention.

To prepare stocks of virus for immunoassay, each virus-producer cell line is grown for short periods (2–3 days) in serum-free medium containing a serum replacement cocktail, for example, 1% Nutridoma-HU (Boeringer-Mannheim) which has a ever, low protein content, or other commercially available serum replacement cocktails. Alternatively, a pre-mixed medium containing the essential serum replacement components and having low protein content (for example OPTI-MEM, GIBCO) may he used.

Cells are removed from the conditioned culture medium, for example by centrifugation. A strong detergent such as Triton®-X (polyethylene glycol p-isooctylphenylether) or Nonidet®P-40 (polyethylene glycol p-ethylphenylether) is then added to the clarified medium. The preferred final concentration of detergent is from about 0.5% to about 1.0%, or that which is known to inactivate the virus's infectivity. After at least 30 minutes at room temperature, the fluid may be aliquoted and stored. The preferred storage temperature is approximately −20° C.

Lectin-Coated Plastic Surfaces

Surfaces forming the assay matrix are passively coated with a ligand that will selectively and stably immobilize the viral glycoproteins but not other components of the virus, which are released into the serum-free medium by the detergent treatment. The ability to selectively immobilize viral glycoproteins assures that when used in the solid phase immunoassay, the antibodies that are detected are specific for the viral glycoproteins.

The preferred ligand to passively coat the surfaces is a lectin; most preferred is the lectin Concanavalin-A (Con-A), an inexpensive plant lectin which binds glycoproteins via the mannosyl residues of their carbohydrate moieties. Con-A has a general specificity for carbohydrates, but will bind a large array of varied glycoproteins and is particularly useful for binding viral envelope glycoproteins.

The assay surface may be plastic, glass, mitrocellulose, nylon, or other surface which may be coated with lectin and used in the immunoassay. Assay surfaces such as the wells of 96 well plates made of specially formulated polystyrene (Immulon II), polyvinylchloride (PVC), and the like plastic may be coated with lectin by applying to the surface a solution containing from about 50 ug/ml to about 200 ug/ml of the lectin. The lectin may be dissolved in a neutral or slightly alkaline buffer comprising water, saline, and phosphate (PBS). Other suitable buffers would include those comprising approximately 10–100 mM HEPES, Tris, or sodium bicarbonate. After incubating the assay surface with the lectin solution for approximately 1 hour at room temperature, the surface is washed 3–4 times with an appropriate wash solution, such as PBS containing a detergent such as 0.1% Tritone®-X100 (polyethylene glycol p-isooctylphenylether), Nonidet®P-40 (polyethylene glycol p-ethylphenylether), Tween®20 (polyoxyethylene (20) sorbitan monolaurate) and the like detergents. Washing is accomplished, for example using any available apparatus for washing a 96 well assay plate.

Viral glycoproteins may be directly added to the washed, lectin coated surfaces. Alternatively, the lectin coated surface may be washed briefly with pure water to remove salts, thoroughly drained and dried under vacuum for approximately 8–24 hours at 4° C. The dried, coated surface may be stored under vacuum or sealed and stored at 4° C. for immobilization of glycoproteins at a later time.

Immobilizing Viral Glycoproteins

Viral glycoproteins are immobilized on lectin-coated surfaces by incubating the viral glycoproteins with the lectin-coated surface at a glycoprotein concentration and for a period of time sufficient to effect immobilization. In general, the period of time will be approximately 5 minutes to one hour.

In the preferred method, the viral glycoproteins are detergent-solubilized prior to immobilization. In the most preferred method the viral glycoproteins are obtained by detergent solubilization of conditioned medium from virus-infected cell culture.

An essential feature of the method of the invention is that by selectively immobilizing viral glycoproteins on lectin-coated surfaces, crude virus-containing fluids from cell cultures grown in serum-free medium can be used as the source of antigen without having to first purify and concentrate the virus. In effect, the system affinity purifies the viral glycoprotein antigens in situ. The specificity of an immunoassay which utilizes viral antigens immobilized by this method is thus determined by the virus used as the source of the viral glycoproteins.

Lectin-immobilization of virus envelope glycoproteins from serum-free medium may be achieved for many types of enveloped viruses. For example, the method of this invention is useful in the immobilization of human retroviruses, including HIV-1, HIV-2, HTLV-I and HTLV-II, and also herpes viruses and respiratory syncytial virus. In addition, glycoproteins from animal retroviruses, such as ovine visna virus and equine infectious anemia virus may be immobilized by this method. The method is not useful for non-enveloped viruses such as picornaviruses and adenoviruses.

Use in Immunoassay

The optimal concentration of viral antigens to be used in a solid-phase immunoassay is determined empirically by assaying serial dilutions of each stock of virus in a ligand-coated assay. Unoccupied lectin binding sites are blocked with a solution containing an excess of irrelevant glycoproteins, for example, fetal calf serum, ovalbumin, or milk proteins. A measured amount of the test sample or control is incubated with the lectin glycoprotein-immobilized, coated assay surface. After a period of incubation time, a standard marker system is used to detect the presence or the amount of the bound viral antibody. Standard marker systems include enzyme-conjugated, radioactive, or fluorescent marked-antibodies to IgG. Enzyme-conjugated antibodies include, for example, alkaline-phosphatase and peroxidase-conjugated antibodies. Standard procedures are followed to develop the marker and quantitate the bound viral antibodies.

Test fluids include serum, saliva, urine, cerebrospinal fluid, and the like body fluids. Also included are cell and tissue culture fluids, for example lymphoid cells which are cultured to test for in vitro production of antibodies reactive with immobilized viral glycoproteins.

The method of this invention greatly simplifies the preparation of immobilized viral antigens thereby reducing the costs of solid phase immunoassay preparation. In addition, the specificity of the antibodies detected is narrowed to only those which recognize viral glycoproteins, the class of viral antigens generally responsible for stimulating protective immunity to enveloped viruses.

Viral antigens immobilized by the method of this invention have been utilized in immunoassays for the detection of the human retrovirus HIV-1, HIV-2, and HTLV-1. The assays correctly identified sera known to be positive or negative for the viral antibodies with 100% accuracy.

The assay method of the present invention is sensitive and highly specific. For examples, titers of HIV-I specific antibodies present in known positive sera generally exceed 1:8,000 when tested against Con-A immobilized HIV-I glycoproteins. Many known positive sera may be diluted greater than 1:64,00 without reaching an endpoint, or a non-detectable level, in this assay. Background reactivity of this assay method with control antigen immobilized on lectin-coated surfaces is low and does not interfere with interpretation of assay results.

EXAMPLES

Example 1

Coating of Plastic 96-Well Assay Plate with Con-A

A 0.02% solution of Con-A was prepared by dissolving 2 mg of Con-A (Vector Laboratories, Burlingame, Calif.) in phosphate buffered saline (PBS, pH 7.4) containing 1 mM $CaCl_2$. Con-A solution (100µl) was added to each well of an Immulon-II 96-well assay plate (Dynatech, Chantilly, Va.) and incubated 1 hour at room temperature. The plate was washed three times with PBS containing 0.1% Triton®-X100(polyethylene glycol p-isoctylphenlether using a standard ELISA plate washer.

Example 2

Prepartion of HIV-1 Virus

A culture of HTLV-IIIB/H9 was obtained from the American Type Culture Collection (Rockville, Md.). The H9 T cell line was originally derived by Popovic at the National Institutes of Health where it was chronically infected with HTLV-IIIB, the prototype strain of HIV-1. HTLV-IIIB/H9 cells were grown in tissue culture flasks as suspension cultures in RPMI 1640 containing 10% fetal bovine serum, at 37° C. in an humidified atmosphere of 5% $CO_2$. Cells were grown in cell densities ranging from $2 \times 10^5$ to $1.0 \times 10^5$ cells/ml. Cells were fed weekly by removing about ¾ of medium and cells and replacing this volume with fresh, complete medium.

To prepare stocks of culture medium for use as a source of virus antigen, HTLV-IIIB/H9 cells were pelleted by centrifugation for 10 minutes at 200×g. The cells were re-suspended at $5-10 \times 10^5$ cells/ml in serum free RPMI 1640 containing 1% Nutridoma-HU and incubated for 2 days at 37° C. Culture medium was harvested and clarified by centrifugation for 10 minutes at 1500 rpm. To 9.0 ml of the clarified culture medium was added 1.0 ml of 10% Triton®-X 100 (polyethylene glycol p-isooctylphenylether) to make a final concentration of 1% Triton®-X (polyethylene glycol p-isooctylphenylether) therefor. After thoroughly mixing and incubation for at least 30 minutes at room temperature, detergent treated fluids were aliquoted and frozen at −20° C. for later use.

Example 3

Immobilization of HIV-1 Glycoproteins on Con-A Surfaces

The detergent-solublized, serum-free conditioned medium containing viral glycoproteins prepared in Example 2, was diluted 1:2 in PBS containing 0.1% Triton-X. To each Con-A coated well prepared in Example 1 was added 100 µl of the diluted conditioned medium. This solution was incubated with the Con-A coated wells for 1 hour at room temperature. The wells were then washed three times with PBS-Triton®-X (polyethylene glycol p-isooctylphenylether).

Example 4

Detection of Antibodies Reacting with Con-A Immobilized HIV-1 Glycoproteins

Ten human sera, five of which were known to be HIV-1 seropositive and five of which were known to be HIV-1 seronegative, were diluted 1:2,000 in RPMI containing 10% fetal bovine serum and 0.1% Titron®-X (polyethylene glycol p-isooctylphenlether). Diluted test sera were added (100 µl/well) to wells containing Con-A immobilized HIV-1 glycoproteins (prepared by the method of Example 3) or to Con-A coated control wells. Control wells had previously been blocked with 100 µl of 10% fetal bovine serum. After a one-hour incubation period at room temperature, the wells were washed four times with PBS-Titron®-X (polyethylene glycol p-isooctylphenlether). The wells were then reacted with 100 µl peroxidase-conjugated, affinity purified goat antibodies to human IgG (Protos Laboratories, San Francisco, Calif.) diluted in RPMI-10% fetal bovine serum. The wells were again washed four times with PBS-Titron®-X (polyethylene glycol p-isooctylphenlether. A volume of 100 µl of TMB, (tetramethyl-benzidine plus $H_2O_2$) was added to each well as a substrate for the peroxidase enzyme and reacted for 10–15 minutes. The enzyme reaction was stopped by the addition of 100 µl 10% $H_2SO_4$. The intensity of yellow color developed was measured by its optical density at 450 nm using a Titertek ELISA plate reader (Flow Laboratories, McLean, Va.). The results for the sera tested are shown in Table 1. All five HIV-1 positive sera show strong reactivity (high OD) with Con-A immobilized HIV-1 glycoproteins, whereas these same sera showed insignificant reactivity with control wells (Con-A coated wells blocked with fetal calf serum). By contrast, all five HIV-1 seronegative sera showed insignificant reactivity with both viral and control wells.

TABLE 1

Reactivity of HIV-1 Seropositive and Seronegative Human Sera with Con-A Immobilized HIV-1 vs Control

| | Optical Density | |
|---|---|---|
| Sera | HIV-1 | Control |
| HIV-1 Positive | | |
| 1 | 1.942 | 0.415 |
| 2 | 1.979 | 0.212 |

TABLE 1-continued

Reactivity of HIV-1 Seropositive and Seronegative Human Sera with Con-A Immobilized HIV-1 vs Control

| Sera | Optical Density | |
|---|---|---|
| | HIV-1 | Control |
| 3 | 1.707 | 0.122 |
| 4 | 0.819 | 0.125 |
| 5 | 1.489 | 0.114 |
| HIV-1 Negative | | |
| 6 | 0.072 | 0.090 |
| 7 | 0.165 | 0.163 |
| 8 | 0.140 | 0.170 |
| 9 | 0.054 | 0.065 |
| 10 | 0.034 | 0.030 |

Example 5

Detection of HIV-2 and HTLV-I Antibodies in Human Sera

H9 cells chronically and productively infected with either HIV-1 (HTLV-IIIB strain) or HIV-2 (MS strain, obtained from the AIDS Research and Reference Reagent Program, Rockville, Md.) as well as the HTLV-I producer cell line, (MT2) were grown for two days in serum-free medium containing 1% Nutridoma-HU. Following the procedure described for Example 2 stocks of serum-free culture medium containing each virus were treated with 1% PBS-Titron®-X (polyethylene glycol p-isooctylphenlether, aliquoted and stored at −20° C. Each of the virus stocks or control medium was diluted 1:2 in PBS-Titron (polyethylene glycol p-Isooctylphenlether and immobilized on Con-A coated assay wells as described for Example 3.

Four human sera, diluted 1:2000 in PBS-10% FBS were each reacted for one hour at room temperature in the assay wells containing HIV-1, HIV-2, HTLV-I or control antigens. One serum was HIV-1 positive, one was HIV-2 positive, one was HTLV-I positive and one was seronegative for all three viruses.

The bound antibody was then detected with peroxidase-conjugated antibody to human IgG and the TMB substrate by the method as described for Example 4. The color reaction was quantitated as OD at 450 nm.

The results are shown in Table 2. The HIV-1 positive serum reacted only with immobilized HIV-1, likewise, the HIV-2 and HTLV-1 positive sera reacted only with HIV-2 and HTLV-I glycoproteins, respectively. Normal serum did not react with any of the antigens.

TABLE 2

VIRAL ANTIBODIES IN HUMAN SERA (OPTICAL DENSITY, 450 nm)

| Serum | Virus Antigen | | | |
|---|---|---|---|---|
| | HIV-1 | HIV-2 | HTLV-I | Control |
| +HIV-1 | 1.456 | 0.257 | 0.207 | 0.188 |
| +HIV-2 | 0.357 | 1.005 | 0.370 | 0.359 |
| +HTLV-I | 0.241 | 0.342 | 1.332 | 0.289 |
| −Normal serum | 0.150 | 0.177 | 0.163 | 0.146 |

Example 6

Immobilization of the Major Envelope Glycoprotein (gp120) of HIV-1

Two envelope glycoproteins of HIV-1 are gp120 and gp41, the major extracellular glycoprotein and the transmembrane glycoprotein, respectively. These glycoproteins are processed from a larger cellular precursor glycoprotein, gp160 by proteolytic cleavage. The following demonstrates that gp120 present in detergent-solubilized serum free conditioned medium of HIV-1 infected cells is immobilized. on a CON-A coated assay surface and may be used in the method of this invention.

HIV-1 glycoproteins were prepared and immobilized on CON-A coated assay wells as described for Example 3.

A sheep antiserum raised against gp120 was obtained from the AIDS Research and Reference Reagent Program, (ERC Bioservices Corp., 649 Lofstrand Lane, Rockville, Md. 20850). Serial dilutions of this antibody in RPMI-10% FCS were assayed for the presence of viral antibody as described for Example 4. The results shown in Table 3, indicate the sheep anti-gp120 reacted with immobilized HIV-1 glycoproteins but not with the control.

TABLE 3

Sheep Anti-HIV-1 gp120 with HIV-1 Glycoproteins Immobilized in Con-A Coated Wells

| Dilution Sheep anti-gp120 | Optical Density[1] | |
|---|---|---|
| | HIV-1 | Control |
| 1:1000 | 0.600 | 0.161 |
| 1:2000 | 0.439 | 0.097 |
| 1:4000 | 0.306 | 0.067 |

[1]Optical Density measured at 450 nm in Flow Titertek ELISA Plate Reader

What is claimed is:

1. A method for detecting antibodies to a virus comprising the steps of:
   coating an assay surface with a lectin;
   immobilizing viral glycoprotein on the lectin—coated surface;
   incubating a test sample with the immobilized glycoproteins for a time sufficient for anti-virus antibodies present in the test sample to bind the immobilized glycoprotein; and
   adding a marker system to detect anti-virus antibodies bound to the immobilized glycoproteins.

2. The method of claim 1 wherein the virus is an enveloped virus.

3. The method of claim 2 wherein the virus is a retrovirus, herpes virus, or a respiratory syncytial virus.

4. The method of claim 3 wherein the retrovirus is a human retrovirus.

5. The method of claim 4 wherein the human retrovirus is HIV-1, HIV-2, HTLV-I or HTLV-II.

6. The method of claim 3 wherein the retrovirus is a visna virus or an infectious anemia virus.

7. The method of claim 1 wherein the test sample is blood, urine, saliva, cerebrospinal fluid, tears, semen, or tissue culture medium.

8. The method of claim 7 wherein the blood is whole blood, blood sera, or blood plasma.

9. The method of claim 1 wherein the lectin is concanavalin-A.

10. The method of claim 1 wherein the viral glycoproteins are solubilized with a detergent prior to being immobilized.

11. The method of claim 10 wherein the detergent is polyethylene glycol p-isooctylphenylether, polyethylene glycol p-ethylphenylether, or polyoxyethylene (20) sorbitan monolaurate.

12. The method of claim 1 wherein the assay surface is glass, plastic, metal, nylon or nitrocellulose.

13. The method of claim 12 wherein the assay surface is plastic.

14. The method of claim 13 wherein the plastic surface is polystyrene or polyvinylchloride.

15. The method of claim 1 wherein the marker system comprises an anti-Ig-antibody, which antibody is enzyme-conjugated, radioactive, or fluoroescently marked.

16. The method of claim 15 wherein the enzyme-conjugated antibodies are alkaline-phosphatase or peroxidase conjugated antibodies.

17. A method for detecting antibodies to a virus comprising the steps of:

infecting a cell culture with a virus;

incubating said virus-infected cell cultures; in serum-free medium to replicate the virus and accumulate virus in the medium;

removing the conditioned medium containing the accumulated virus;

solubilizing the glycoprotein of the accumulated virus by adding detergent to the removed conditioned medium;

immobilizing the solubilized viral glycoprotein on a lectin-coated assay surface;

incubating a test sample with the immobilized glycoprotein for a time sufficient for anti-viral antibodies present in the test sample to bind the immobilized glycoprotein; and adding a marker system to detect anti-virus antibodies bound to the immobilized glycoprotein.

18. The method of claim 17 wherein the conditioned medium is produced by culturing cells infected with virus in serum-free medium.

19. The method of claim 18 wherein the virus is a retrovirus.

20. The method of claim 19, wherein the retrovirus is HIV-1, HIV-2, HTLV-I or HTLV-II.

21. The method of claim 18 wherein the serum-free medium contains from about 1 to about 20% of a serum replacement.

22. The method of claim 17 wherein the conditioned medium is separated from the infected cells prior to being solubilized.

23. The method of claim 17 wherein the cells are a continuous lymphoid cell line.

24. The method of claim 23 wherein the cell line is H9, CEM, or Molt 4.

25. The method of claim 23 wherein the cell line is MT2 or MO.

26. The method of claim 17 wherein the viral glycoproteins are immobilized by incubating the detergent-solubilized conditioned medium with the lectin-coated surface.

* * * * *